United States Patent
Brand et al.

(10) Patent No.: US 6,768,915 B2
(45) Date of Patent: Jul. 27, 2004

(54) METHOD FOR THE OPERATION OF A MAGNETIC RESONANCE APPARATUS AND MAGNETIC RESONANCE APPARATUS FOR THE IMPLEMENTATION OF THE METHOD

(75) Inventors: Martin Brand, Erlangen (DE); Rainer Kuth, Herzogenaurach (DE)

(73) Assignee: Siemens Aktiengesellschaft, München (DE)

( * ) Notice: Subject to any disclaimer, the term of this patent is extended or adjusted under 35 U.S.C. 154(b) by 122 days.

(21) Appl. No.: 10/027,849

(22) Filed: Dec. 21, 2001

(65) Prior Publication Data
US 2002/0107440 A1 Aug. 8, 2002

(30) Foreign Application Priority Data
Jan. 8, 2001 (DE) .......................... 101 00 441

(51) Int. Cl.⁷ .............................................. A61B 5/055
(52) U.S. Cl. ...................... 600/410; 600/411; 600/413; 324/307; 324/309
(58) Field of Search ................. 600/410, 411, 600/413; 324/307, 309

(56) References Cited

U.S. PATENT DOCUMENTS

| | | | | |
|---|---|---|---|---|
| 5,603,322 A | * | 2/1997 | Jesmanowicz et al. | 600/410 |
| 5,662,112 A | | 9/1997 | Heid | |
| 6,289,234 B1 | * | 9/2001 | Mueller | 600/410 |
| 6,298,258 B1 | | 10/2001 | Heid et al. | |
| 6,430,431 B1 | * | 8/2002 | De Yoe | 600/410 |
| 6,477,399 B2 | * | 11/2002 | Biswal et al. | 600/410 |

FOREIGN PATENT DOCUMENTS

EP        0 630 481        6/1999

* cited by examiner

Primary Examiner—Ruth S. Smith
(74) Attorney, Agent, or Firm—Schiff Hardin LLP

(57) ABSTRACT

In a method for the operation of a magnetic resonance apparatus, a prescribable event that can trigger a neural activity of an examination subject is initiated, the implementation of the event and the readiness of the examination subject to perceive the event that triggers the neural activity are monitored, and given a positive result of the monitoring, an image dataset of a region of the examination subject to be imaged, and to which the event can be allocated, is registered.

28 Claims, 2 Drawing Sheets

| No. | Prescribed image dataset with/without neural activity | Result of the monitoring |
|---|---|---|
| ... | | ... |
| 101 | with neural activity | positive |
| 102 | with neural activity | positive |
| 103 | with neural activity | positive |
| 104 | with neural activity | negative |
| 105 | with neural activity | positive |
| 106 | without neural activity | positive |
| 107 | without neural activity | positive |
| 108 | without neural activity | positive |
| 109 | without neural activity | positive |
| 110 | without neural activity | negative |
| 111 | with neural activity | negative |
| 112 | with neural activity | positive |
| ... | | |

METHOD FOR THE OPERATION OF A MAGNETIC RESONANCE APPARATUS AND MAGNETIC RESONANCE APPARATUS FOR THE IMPLEMENTATION OF THE METHOD

BACKGROUND OF THE INVENTION

1. Field of the Invention

The present invention is directed to a method for the operation of a magnetic resonance apparatus and to a magnetic resonance apparatus for the implementation of the method.

2. Description of the Prior Art

Magnetic resonance technology is a known technique for producing images of the inside of the body of an examination subject. To that end, rapidly switched gradient fields are superimposed on a static basic magnetic field in a magnetic resonance apparatus. For triggering magnetic resonance signals, radio-frequency signals are emitted into the examination subject, and the magnetic resonance signals that are triggered thereby are registered and image datasets and magnetic resonance images are produced on the basis thereof.

In general in the medical field, all methods that use a repeated scanning of a structure of organs and tissues in order to image temporally changing processes such as physiological functions or pathological events are referred to as functional imaging. This term has a narrower meaning in the context magnetic resonance techniques, namely methods that make it possible to identify and image the cerebral sulci in the nervous system, particularly cerebral sulci of a patient, that are stimulated by sensory stimuli and/or by a motor, sensory or cognitive task. Such stimuli can be, for example, acoustic or visual stimuli. In the simplest case, one of the motor tasks can be a defined movement, for example a movement of the hand or a finger.

The BOLD effect (blood oxygen level dependent) is thereby the basis of functional magnetic resonance imaging. The BOLD effect is based on the fact that oxygenated and de-oxygenated hemoglobin in the blood have different magnetic properties. An intensified neural activity in the brain is thereby locally associated with an increased delivery of oxygenated blood, this effecting a corresponding increase in intensity at the location in a magnetic resonance image generated with a gradient echo sequence. The BOLD effect occurs with a time delay of a few seconds following an event that triggers the neural activity.

In functional magnetic resonance imaging, for example, three-dimensional image datasets of the brain are registered every two through four seconds, for example with an echo planar method. Echo planar methods have the advantage that the image dataset registration—with fewer than 100 ms required for an individual, three-dimensional image dataset—is very fast. Image datasets with or without a specific neural activity are thereby registered at different points in time. For producing a functional image, the image datasets registered with the neural activity are compared for signal differences to those without the neural activity, to identify active brain areas. To ensure that the functional image contains the desired functional information, the respective image datasets registered with the neural activity and the image datasets registered without the neural activity are averaged, for example before the comparison, due to the fact that the BOLD effect is comparatively weak in terms of being able to be registered by magnetic resonance technology. This reduces the probability of correctly determining whether a particular image dataset was registered with or without neural activity, or requires that a number of image datasets be registered in order to arrive at a functional information having the same correctness probability. The latter, among other things, causes an undesired lengthening of the examination time.

SUMMARY OF THE INVENTION

An object of the present invention is to provide an improved method for the operation of a magnetic resonance apparatus as well as a magnetic resonance apparatus for the implementation of this method with which, among other things, functional information having a high correctness probability can be acquired in a time-efficient way.

This object is achieved in accordance with the invention in a first embodiment of a method for the operation of a magnetic resonance apparatus wherein a prescribable event that can trigger a neural activity of an examination subject is initiated, the implementation of the event and the readiness of a sensory receptor of the examination subject for the event that triggers the neural activity are monitored, and given a positive result of the monitoring, an image dataset of a region of the examination subject, to which the event can be allocated, is registered.

This object is achieved in a second embodiment of a method for the operation of a magnetic resonance apparatus wherein image datasets of a region of an examination subject to be imaged and to which a prescribable neural activity is to be allocated are registered, whereby the activity can have an event allocated to it that can trigger the activity, an occurrence of the event and the readiness of a sensory receptor of the examination subject for the event triggering the activity are monitored, a result of the monitoring is allocated to the respective image dataset, and image datasets to which a positive result is allocated are further-processed in common.

Compared to a conventional magnetic resonance imaging wherein image datasets for which a clear decision cannot be made as to whether they contain neural activity nevertheless processed for identifying a functional information, the inventive method achieves a higher correctness probability of the functional information given the same number of image datasets, or the functional information can be acquired with the same correctness probability and fewer image datasets, and thus in a more time-efficient way.

By registering and recording the readiness of the subject for reactions to and/or interactions with the event, for example, in the framework of functional magnetic resonance imaging, only those image datasets are further-processed that are unambiguously correlated with the reaction and/or interaction of the patient. As a result, the method can also be particularly utilized in a functional magnetic resonance examination of infirm patients from whom the willingness to cooperate that is required for interaction of the patient cannot always be counted on, or cannot be counted on for the entire duration of the examination.

DESCRIPTION OF THE DRAWINGS

FIG. 2 is a table to be occupied in the course of a functional magnetic resonance imaging procedure in accordance with the invention.

DESCRIPTION OF THE PREFERRED EMBODIMENTS

Figure 1:
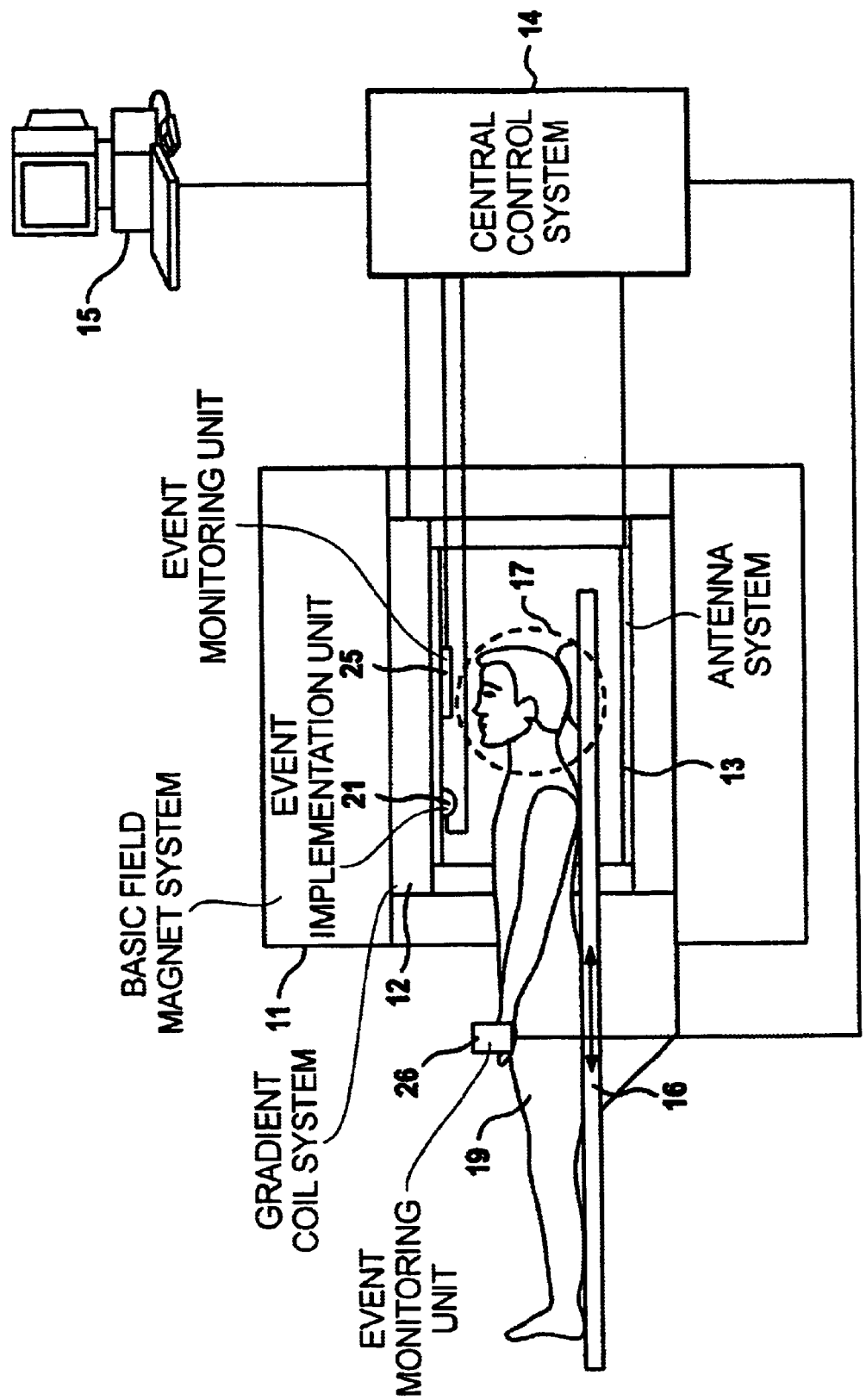
FIG. 1 is a side view of a magnetic resonance apparatus for implementing the inventive method.

As an exemplary embodiment of the invention, FIG. 1 shows a magnetic resonance apparatus that is equipped and is operable in conformity with the invention. The magnetic resonance apparatus has a basic field magnet system 11 for generating a basic magnetic field and a gradient coil system 12 for generating gradient fields. Further, the magnetic resonance apparatus has an antenna system 13 with which radio-frequency signals can be emitted into a patient 19 as the examination subject for triggering magnetic resonance signals and with which the triggered magnetic resonance signals are registered. The patient 19 is placed on a movable support 16. The gradient coil system 12 as well as the antenna system 13 are connected to a central control system 14. The central control system 14 controls currents in the gradient coil system 12 on the basis of a selected sequence as well as controlling the radio-frequency signals that are emitted according to the selected sequence, as well as for further-processing and storing the magnetic resonance signals registered by the antenna system 13. Further, the central control system 14 is connected to a display and operating unit 15 via which inputs of an operator, for example the desired sequence type and sequence parameters, are supplied to the central control system 14. Among other things, the magnetic resonance images that are generated are also displayed at the display and operating unit 15.

At the beginning of a functional magnetic resonance imaging procedure, the patient 19 is placed on the support 16 which has been withdrawn as far as possible from the basic field magnet system 11. According to the requirements of functional magnetic resonance imaging wherein a head of the patient 19 represents the region to be imaged, the patient 19 is placed head first on the support 16. Subsequently, the support 16 is displaced such that the head is positioned in the imaging volume 17 of the magnetic resonance apparatus.

After this positioning, image datasets with and without a specific neural activity are to be registered for generating a functional image of the brain of the patient 19, these image datasets being compared to one another for signal differences in order to identify active cerebral sulci. Many image datasets with and without the neural activity are thereby registered and subsequently subjected to an averaging so that it is assured that the functional image contains a functional information in view of the neural activity. This is necessary because the neural activity produces only comparatively weak signal differences due to the BOLD effect. The neural activity is initiated by a prescribable event. For example, an attempt is made to stimulate a sensory organ of the examination subject with the event. The magnetic resonance apparatus for this purpose has an event implementation unit 21 that is connected to the central control system 14. In one embodiment, the event implementation unit 21 is fashioned as an optical output device with which visual stimulation of the patient 19 is possible on the basis of a light signal.

The magnetic resonance apparatus further has a first event monitoring unit 25 with which the implementation of the event the readiness of the patient 19 to perceive the event triggering the neural activity is monitored. Given fashioning of the event implementation unit 21 as an optical output device for visual stimulation of the patient 19, the first event monitoring unit 25 is fashioned to monitor both an output of the light signal as well as whether the eyes of the patient 19 are open or shut. An influence of the optical signal on the patient 19 that triggers the neural activity is only assured given an output of the light signal and open eyes on the part of the patient 19. When the aforementioned monitoring leads to a positive event in the aforementioned sense, then this is correspondingly noted for the image dataset that is registered following the light signal. For that purpose, the first event monitoring unit 25 is connected to the central control system 14.

Conversely, of course, an intentional non-implementation of the event for image datasets without the neural activity also can be monitored.

FIG. 2 shows a table 30 that is filled during the course of a functional magnetic resonance imaging. A number and an entry as to whether the image dataset is to be registered with or without the neural activity are thereby entered in the table 30 for an image dataset to be registered. Further, whether the event that can trigger the neural activity was in fact implemented before the registration of the image dataset and/or whether an influence of the event triggering the neural activity occurred, are also noted in the table 30. The procedure when filling the table 30 is described as an example in the embodiment for visual stimulation of the patient 19 described in FIG. 1. The table 30 is stored in the central control system 14.

An image dataset with which neural activity that is triggered by the visual stimuli is thereby indicated with the number 101 in the table 30 of FIG. 2. To that end, the event implementation unit 21 is driven by the central control system 14 to emit a light signal. In response thereto, the event implementation unit 21 emits the corresponding light signal. The first event monitoring unit 25 acquires the output of the light signal and simultaneously acquires the eyes of the patient 19 as being open and reports this to the central control system 14. The report indicates that the output of the light signal has been implemented as the event and the light signal was capable of triggering neural activity because the eyes of the patient 19 were open. Accordingly, the central control system 14 notes the positive monitoring event at the number 101 in the table 30. After a prescribable time of, for example, a few seconds has passed since the output of the light signal, the actual image dataset for number 101 is registered and stored in the central control system 14. A three-dimensional image dataset of the brain of the patient 19 is generated for this purpose, for example with an echo planar method. The length of the time lapse is essentially defined by the time delay between the event triggering the neural activity and an expected maximum of the BOLD effect in the brain of the patient 19.

After another prescribable time lapse of, for example, a few seconds, a further image dataset with neural activity is to be registered under number 102. A procedure that is analogous to that for image dataset number 101 thereby ensues. The same is also true for the image datasets of number 102 and number 103.

A further image dataset with the neural activity allocated to number 104 is to be registered. To that end, the event implementation unit 21 again emits a light signal. Upon emission of the light signal, the first event monitoring unit 25 registers that the eyes of the patient 19 are closed and reports this to the central control system 14. Since the light signal could not trigger the neural activity, a negative monitoring result is noted for number 104. The image dataset belonging to number 104 is then registered and stored in conformity with the prescribable time lapse. In another embodiment, the appertaining image dataset is not produced at all given a negative monitoring result; rather, the procedure continues with the preparation and the registration of the image dataset belonging to the next number.

An image dataset having the neural activity corresponding to number 101 is registered again with number 105.

Image datasets without neural activity are to be registered with number 106 through number 110. The task of the first event monitoring unit 25 is to monitor that no light signal is emitted by the event implementation unit 21 in a prescribable time span before the registration of the image datasets. For the image datasets number 106 through number 109, the first event monitoring unit 25 does not detect any preceding emission of a light signal and reports this to the central control system 14, so that a positive event is respectively allocated to number 106 through number 109. At number 110, a light signal is mistakenly emitted before the registration of the image dataset. This is registered by the first event monitoring unit 25 and is reported to the central control system 14 and is allocated to number 110 as a negative monitoring event.

An image dataset with the neural activity is to be registered again allocated to number 111. To that end, the event implementation 21 is driven by the central control system 14 to output a light signal. For whatever reasons, however, the event implementation unit 21 does not emit a corresponding light signal. The first event monitoring unit 25 registers the non-output of the light signal and reports this to the central control system 14, where a negative event is entered at number 111. Corresponding to the prescribable time lapse, the image dataset belonging to number 111 is registered after the actuation of the event implementation unit 21. In the other embodiment, the appertaining image dataset is not produced at all as a consequence of the negative monitoring result; rather, the procedure continues with the preparation and the registration of the image dataset belonging to the next number.

An image dataset with the neural activity corresponding to number 101 is then again registered with number 112, etc.

For forming functional magnetic resonance images, the image datasets registered with neural activity are to be compared for signal differences to those without neural activity. Only those image datasets to which a positive monitoring result is allocated according to table 30 of FIG. 2 are employed in this comparison. The comparison can be implemented both after the end of a registration of all image datasets as well as from image dataset registration-to-image dataset registration.

In another embodiment, the event implementation unit 21 of FIG. 1, as an optical output device, is utilized to request that the patient 19 carry out a declared task of, for example, a motor or cognitive type with the emission of the light signal. In yet another embodiment, the event implementation unit 21 is fashioned, for example, as an acoustic output device for stimulating the hearing of the patient 19. In another embodiment, the event implementation unit 21 can be arranged in contact with the skin of the patient 19, so that sensory perceptions via the skin of the patient 19 can be stimulated therewith.

Alternatively or in addition to the aforementioned first event monitoring unit 25, the magnetic resonance apparatus of FIG. 1 can have a second event monitoring unit 26 that is likewise connected to the central control system 14. In one embodiment, the second event monitoring unit 26 is essentially fashioned as an electrical push button that the patient 19 can actuate with finger pressure. Using, for example, the event implementation unit 21 in an embodiment as an acoustic output device, the patient 19 is thereby acoustically requested to actuate the push button as a motor task. The second event monitoring unit 26 monitors the execution of the finger motion of the patient 19 as the event triggering the neural activity. The pressing or non-pressing of the push button by the patient 19 is registered in the central control system 14 and is correspondingly allocated to a subsequently registered image dataset as positive or negative event of the monitoring. In an augmented embodiment, the first event monitoring unit 25, when it is fashioned in a corresponding way, monitors the implementation of the acoustic signal and reports an implementation or non-implementation of the acoustic signal to the central control system 14, this also being taken into consideration in the central control system 14 when allocating a positive or negative event.

In another embodiment, the influence of the event triggering the neural activity is verified by measuring brain currents of the patient.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating a magnetic resonance apparatus, comprising the steps of:
    (a) implementing a prescribable event which is capable of triggering neural activity in an examination subject;
    (b) electronically monitoring implementation of said event and a sensory receptor of the examination subject for said event, to obtain one of a positive result indicating the examination subject is capable of perceiving said event or a negative result indicating the examination subject is not capable of perceiving said event; and
    (c) only given a positive result, electronically enabling a magnetic resonance imaging scan of a region of said subject in which said neural activity is expected to be conducted, to obtain an image dataset of said region, and storing said image dataset.

2. A method as claimed in claim 1 wherein, given a negative result in said monitoring step, repeating at least steps (a) and (b).

3. A method as claimed in claim 1 wherein step (a) comprises implementing a prescribable event which stimulates at least one sensory organ of said examination subject.

4. A method as claimed in claim 1 wherein step (a) comprises causing said examination subject to execute a task selected from the group consisting of motor tasks, sensory tasks and cognitive tasks.

5. A method as claimed in claim 1 wherein step (c) comprises conducting said magnetic resonance imaging scan of a region of said examination subject containing at least a portion of the central nervous system.

6. A method as claimed in claim 1 wherein step (c) comprises conducting said magnetic resonance imaging scan after a predetermined time lapse following implementation of said event in step (a).

7. A method as claimed in claim 1 comprising the additional steps of:
    conducting at least one further magnetic resonance imaging scan of said examination subject to obtain at least one further image dataset of said region without implementing said event; and
    comparing said image dataset of said region obtained in step (c) with said at least one further image dataset to identify a neurally active region of said examination subject.

8. A method for operating a magnetic resonance apparatus, comprising the steps of:
    (a) implementing a prescribable event which is capable of triggering neural activity in an examination subject;
    (b) electronically monitoring implementation of said event and a sensory receptor of the examination subject for said event, to obtain one of a positive result indicating the examination subject is capable of perceiving said event or a negative result indicating the examination subject is not capable of perceiving said event;

(c) conducting a magnetic resonance imaging scan of a region of said subject in which said neural activity is expected, to obtain an image dataset of said region;

(d) storing said image dataset with an indication of said positive result or said negative result allocated thereto;

(e) repeating steps (a), (b), (c) and (d) to obtain a plurality of image datasets; and (f) further processing, in common, only image datasets among said plurality of image datasets which have said positive result allocated thereto.

9. A method as claimed in claim 8 wherein step (f) comprises averaging said image datasets which have said positive result allocated thereto.

10. A method as claimed in claim 8 wherein step (a) comprises implementing a prescribable event which stimulates at least one sensory organ of said examination subject.

11. A method as claimed in claim 8 wherein step (a) comprises causing said examination subject to execute a task selected from the group consisting of motor tasks, sensory tasks and cognitive tasks.

12. A method as claimed in claim 8 wherein step (c) comprises conducting said magnetic resonance imaging scan of a region of said examination subject containing at least a portion of the central nervous system.

13. A method as claimed in claim 8 wherein step (c) comprises conducting said magnetic resonance imaging scan after a predetermined time lapse following implementation of said event in step (a).

14. A method as claimed in claim 8 comprising the additional steps of:

conducting at least one further magnetic resonance imaging scan of said examination subject to obtain at least one further image dataset of said region without implementing said event; and comparing said image dataset of said region obtained in step (c) with said at j) least one further image dataset to identify a neurally active region of said examination subject.

15. A magnetic resonance imaging apparatus comprising:

an event implementation unit which implements a prescribable event which is capable of triggering neural activity in an examination subject;

a monitoring unit which electronically monitors implementation of said event and a sensory receptor of the examination subject for said event, to obtain one of a positive result indicating the examination subject is capable of perceiving said event or a negative result indicating the examination subject is not capable of perceiving said event; and a magnetic resonance scanner having a control unit which, only given a positive result, electronically enables the scanner to conduct a magnetic resonance imaging scan of a region of said subject in which said neural activity is expected, to obtain an image dataset of said region, and having a memory for storing said image dataset.

16. A magnetic resonance imaging apparatus as claimed in claim 15 wherein, given a negative result, said implementation unit again implements said prescribable event, and said monitoring unit again obtains one of said positive result or said negative result.

17. A magnetic resonance imaging apparatus as claimed in claim 15 wherein said event implementation unit implements a prescribable event which stimulates at least one sensory organ of said examination subject.

18. A magnetic resonance imaging apparatus as claimed in claim 15 wherein said event implementation unit allows said examination subject to execute a task selected from the group consisting of motor tasks, sensory tasks and cognitive tasks.

19. A magnetic resonance imaging apparatus as claimed in claim 15 wherein said magnetic resonance scanner conducts said magnetic resonance imaging scan of a region of said examination subject containing at least a portion of the central nervous system.

20. A magnetic resonance imaging apparatus as claimed in claim 15 wherein said magnetic resonance scanner conducts said magnetic resonance imaging scan after a predetermined time lapse following implementation of said event.

21. A magnetic resonance imaging apparatus as claimed in claim 15 wherein said magnetic resonance scanner conducts at least one further magnetic resonance imaging scan of said examination subject to obtain at least one further image dataset of said region without implementing said event, and compares said image dataset of said region with said at least one further image dataset to identify a neurally active region of said examination subject.

22. A magnetic resonance imaging apparatus comprising:

an event implementation unit which implements a prescribable event which is capable of triggering neural activity in an examination subject;

a monitoring unit which electronically monitors implementation of said event and a sensory receptor of the examination subject for said event, to obtain one of a positive result indicating the examination subject is capable of perceiving said event or a negative result indicating the examination subject is not capable of perceiving said event;

a magnetic resonance scanner which conducts a magnetic resonance imaging scan of a region of said subject in which said neural activity is expected, to obtain an image dataset of said region, stores said image dataset with an indication of said positive result or said negative result allocated thereto, enables said event implementation unit to repeatedly implement said prescribable event, each prescribable event being monitored by said monitoring unit and after which said scanner conducts a further scan of said region to obtain a plurality of image datasets, and further processes, in common, only image datasets among said plurality of image datasets which have said positive result allocated thereto.

23. A magnetic resonance imaging apparatus as claimed in claim 22 wherein said scanner averages said image datasets which have said positive result allocated thereto.

24. A magnetic resonance imaging apparatus as claimed in claim 22 wherein said event implementation unit implements a prescribable event which stimulates at least one sensory organ of said examination subject.

25. A magnetic resonance imaging apparatus as claimed in claim 22 wherein said event implementation unit allows said examination subject to execute a task selected from the group consisting of motor tasks, sensory tasks and cognitive tasks.

26. A magnetic resonance imaging apparatus as claimed in claim 22 wherein said magnetic resonance scanner conducts said magnetic resonance imaging scan of a region of said examination subject containing at least a portion of the central nervous system.

27. A magnetic resonance imaging apparatus as claimed in claim 22 wherein said magnetic resonance scanner conducts said magnetic resonance imaging scan after a predetermined time lapse following implementation of said event.

28. A magnetic resonance imaging apparatus as claimed in claim 22 wherein said magnetic resonance scanner conducts at least one further magnetic resonance imaging scan of said examination subject to obtain at least one further image dataset of said region without implementing said event, and compares said image dataset of said region with said at least one further image dataset to identify a neurally active region of said examination subject.

* * * * *